(12) United States Patent
Clarke et al.

(10) Patent No.: US 6,449,827 B1
(45) Date of Patent: Sep. 17, 2002

(54) APPARATUS FOR GRIPPING MICROPLATES

(75) Inventors: Glenn A. Clarke, Flemington; Marc N. Feiglin, East Brunswick; Gary S. Kath, Scotch Plains; Gregory W. King, Carteret, all of NJ (US)

(73) Assignee: Merck & Co., Inc, Rahway, NJ (US)

( * ) Notice: Subject to any disclaimer, the term of this patent is extended or adjusted under 35 U.S.C. 154(b) by 71 days.

(21) Appl. No.: 09/686,645

(22) Filed: Oct. 10, 2000

Related U.S. Application Data
(60) Provisional application No. 60/161,216, filed on Oct. 22, 1999.

(51) Int. Cl.[7] .............................................. B23Q 7/00
(52) U.S. Cl. ........................... 29/559; 29/283; 269/303; 269/309; 269/318
(58) Field of Search ........................... 29/559, 801, 283, 29/DIG. 44

(56) References Cited

U.S. PATENT DOCUMENTS 4,403,567 A * 9/1983 DeCosta et al. .............. 269/21
6,164,633 A * 12/2000 Mulligan et al. ............. 269/21

FOREIGN PATENT DOCUMENTS

| DE | 003208864 A1 | * 9/1983 | ................... 269/21 |
| JP | 404322920 A1 | * 11/1992 | ................... 29/559 |
| JP | 406008085 A1 | * 1/1994 | ................... 269/21 |

* cited by examiner

Primary Examiner—David P. Bryant
Assistant Examiner—Jermie E. Cozart
(74) Attorney, Agent, or Firm—James M. Hunter, Jr.; Mark R. Daniel

(57) ABSTRACT

An apparatus suitable for securely gripping and holding a microplate or other containers during robotic de-lidding operations. A microplate placed on the apparatus is held by a vacuum drawn through the base thereof, allowing the lid of the microplate to be removed without movement of the plate. Afterwards, the vacuum can be discontinued and the plate removed from the apparatus.

20 Claims, 4 Drawing Sheets

APPARATUS FOR GRIPPING MICROPLATES

This application claims the benefit of U.S. Serial No. 60/161,216, filed Oct. 22, 1999;

BACKGROUND OF THE INVENTION

Microplates, sometimes referred to as micro-titer plates, are generally utilized in the performance of biological assays, wherein the effects of a drug, bacteria or virus on living cells is characteristized, e.g. toxicity, metabolism, etc. Microplates are also utilized to store chemical compounds. More particularly, biological assays are utilized to determine the inter-reaction of pharmaceutical compositions.

Due to the vast amount of pharmaceutical drug candidates under evaluation as well as the abundance of assays performed to determine the activity and safety of a drug candidate, microplates will generally contain a large matrix of sample collection wells. For example, the microplates can be arranged in matrices of 5×6, 6×8, 8×10, 8×12, etc. After samples are collected in microplate wells, a lid is generally placed thereupon to prevent evaporation and contamination, and the microplate can be held in cold storage until ready for screening.

Today, computer-controlled processes and robotics are available to manage every facet of collecting, storing and screening biological assays. Heretofore, robotic de-lidding of a microplate, after removal from cold storage and/or prior to sample analysis, has presented several problems. Associated with the de-lidding operation has been the problem of providing an automated apparatus for holding a microplate while removing the lid and immediately releasing it thereafter, so that a robotic mechanism can deliver the microplate to a screening station.

The present invention provides an apparatus that can be automated for utilization with robotic handling systems to securely grip and hold a container such as a microplate during lid removal, mixing or oscillation operations. As will become apparent to those skilled in the art, the apparatus of the invention can also be adapted to grip and hold a variety of containers, e.g. microplates, jars, vials, dishes, etc., while removing lids, rotating, oscillating, agitating, removing samples therefrom, and other operations as will become apparent to those skilled in the art.

SUMMARY OF THE INVENTION

An apparatus for gripping and holding a container during de-lidding, mixing or oscillating operations, comprising:
 a) a horizontally positioned, flat surfaced base comprising: i) a vertical aperture partially extending through the top of the base, ii) a horizontal aperture extending through a side of the base and intersecting the vertical aperture, iii) a plurality of intermittent, vertical, raised edges on the top of the base, and iv) means for attaching the base to a support;
 b) a flat, elastic plate gasket, conforming to the shape of the base, resting on top of the base between the raised edges, the gasket having a vertical aperture therethrough aligning with the vertical aperture of the base, wherein the height of the raised edges extend above the height of the plate gasket; and
 c) vacuum means attached to the horizontal aperture on the side of the base,
 wherein a flat, bottom container having a lid thereon and conforming to the shape of the base being placed on top of the plate gasket, fitting within and abutting against the raised edges of the base, and a vacuum being applied to the base, the container is suctionally pulled down towards the base and securely held there without loss of vacuum while means for removing the lid is being applied thereto.

DETAILED DESCRIPTION OF THE INVENTION

The invention described herein is a static apparatus for gripping and securely holding a microplate during an automated or robotic process of removing a lid from the top of the plate to expose fluid samples in the wells of the plate. The shape of the apparatus will generally conform to the shape of a microplate, e.g. square, oval or rectangular. Typically, the shape of a microplate will be square or rectangular.

Figure 1:
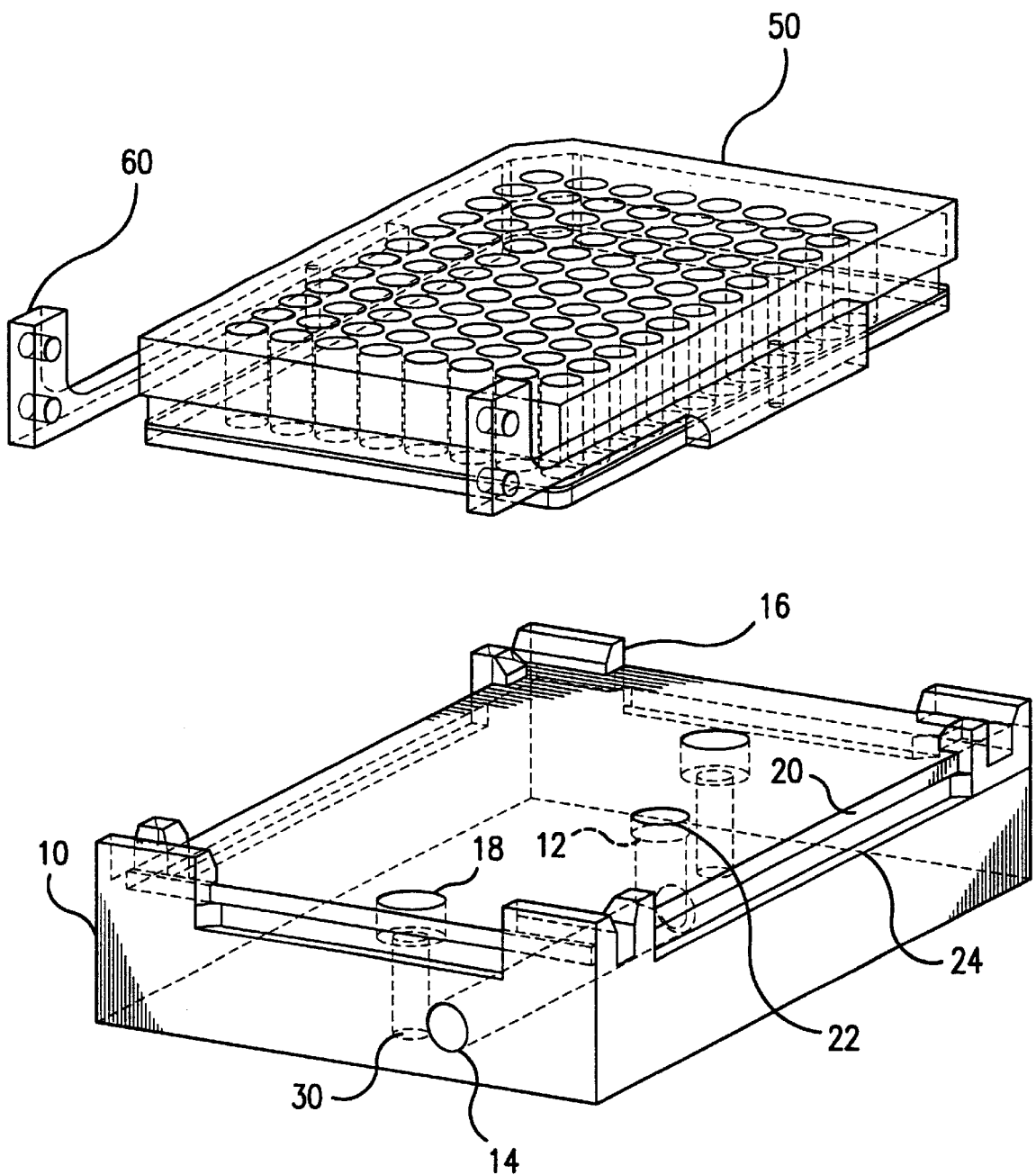
FIG. 1 is an isometric view in elevation of the microplate gripping apparatus illustrating a lidded microplate being held by robotic fingers, wherein the microplate is aligned with and positioned above the apparatus.

Referring to FIG. 1, the apparatus for gripping and securely holding a rectangular-shaped, microplate during robotic de-lid operations can be characterized as:
 a) a horizontally positioned, rectangular-shaped, flat-top base 10 comprising: i) a centrally positioned, vertical aperture 12 partially extending through the top of the base, ii) a horizontal aperture 14 partially extending through a side of the base and intersecting the vertical aperture to form a conduit, iii) vertical, raised edges 16 proximal to the corners of the top of the base, and iv) means for attaching 18 the base to a support, e.g. a chemical adherent, bolts and nuts, screws or clamps;
 b) a flat, rectangular-shaped, elastic, plate gasket 20 resting on top of the base 10 having a vertical aperture 22 therethrough aligning with the vertical aperture 12 of the base, wherein the shape of the plate gasket conforms to and fits within the shape of the base, the height of the raised edges 16 extending above the height of the plate gasket, wherein horizontal, outer ledges 24 are formed along the sides of the base between the vertical edge of the plate gasket and the vertical edge of the base; and
 c) vacuum means 30 attached to the horizontal aperture on the side of the base,
 wherein a lidded, flat, bottom microplate, the lid 50 having bottom edges protruding from the side of the plate, the plate being held on opposing sides by robotic, fingers 60, the microplate being placed on top of the plate gasket, the bottom of the fingers proximal on the ledge of the base, the microplate fitting within and abutting against the raised edges, a vacuum being drawn on base, the microplate being suctionally pulled towards the base and securely held there without loss of vacuum, the robotic fingers releasing the microplate, and the fingers being raised to contact the protruding, bottom edges of the lid, and the fingers being raised to remove the lid.

Figure 2:
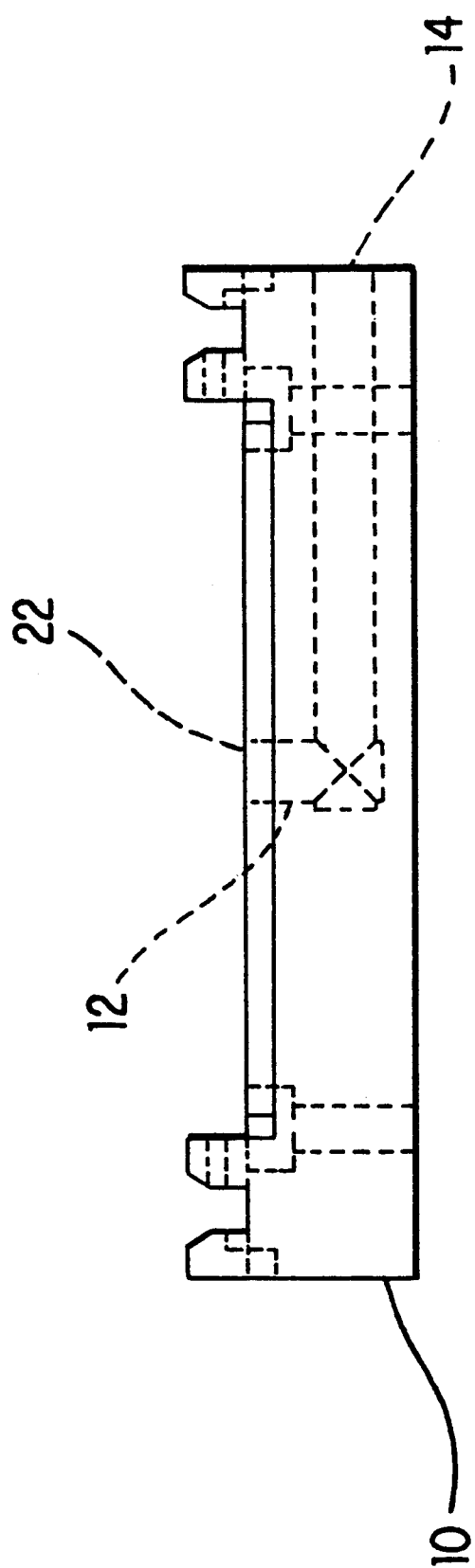
FIG. 2 is a side view in elevation of the the microplate gripping apparatus illustrating aligned vertical apertures through the base and plate gasket, and a horizontal aperture through the base that intersects with the vertical aperture of the base.

Referring to FIG. 2, a side view in elevation of the microplate gripping apparatus 10 illustrating the conduit utilized for applying the vacuum means formed by vertical aperture 12 and horizontal aperture 14 extending through the base is shown. More particularly, the horizontal aperture is bored through a side of the base, extending partially through, and intersects the vertical aperture bored through the top of the base, extending partially therethrough. The two apertures intersect to form a conduit having a first end on the top of the base and a second end on the side of the base. To the side aperture, the vacuum means, in the form of a vacuum pump or other vacuum device can be connected. The plate gasket also has vertical aperture 22 completely bored therethrough, wherein the aperture aligns with the horizontal aperture of the base. The vacuum means can be automatically controlled by a solenoid valve programmed to operate in sequence with the robotic fingers. That is, the solenoid valve can be timed to apply a vacuum after the microplate has been placed on the apparatus, and release the vacuum after the fingers have removed the lid of the microplate. Once the vacuum means is applied to the apparatus, a flat, bottom microplate placed between the raised edges onto the plate gasket will be suctionally held in place by a vacuum force. The vacuum force actually pulls the plate onto the plate gasket, wherein the elastic material of the plate gasket compresses, wherein none of the vacuum is lost and the microplate is gripped and held securely.

Figure 3:
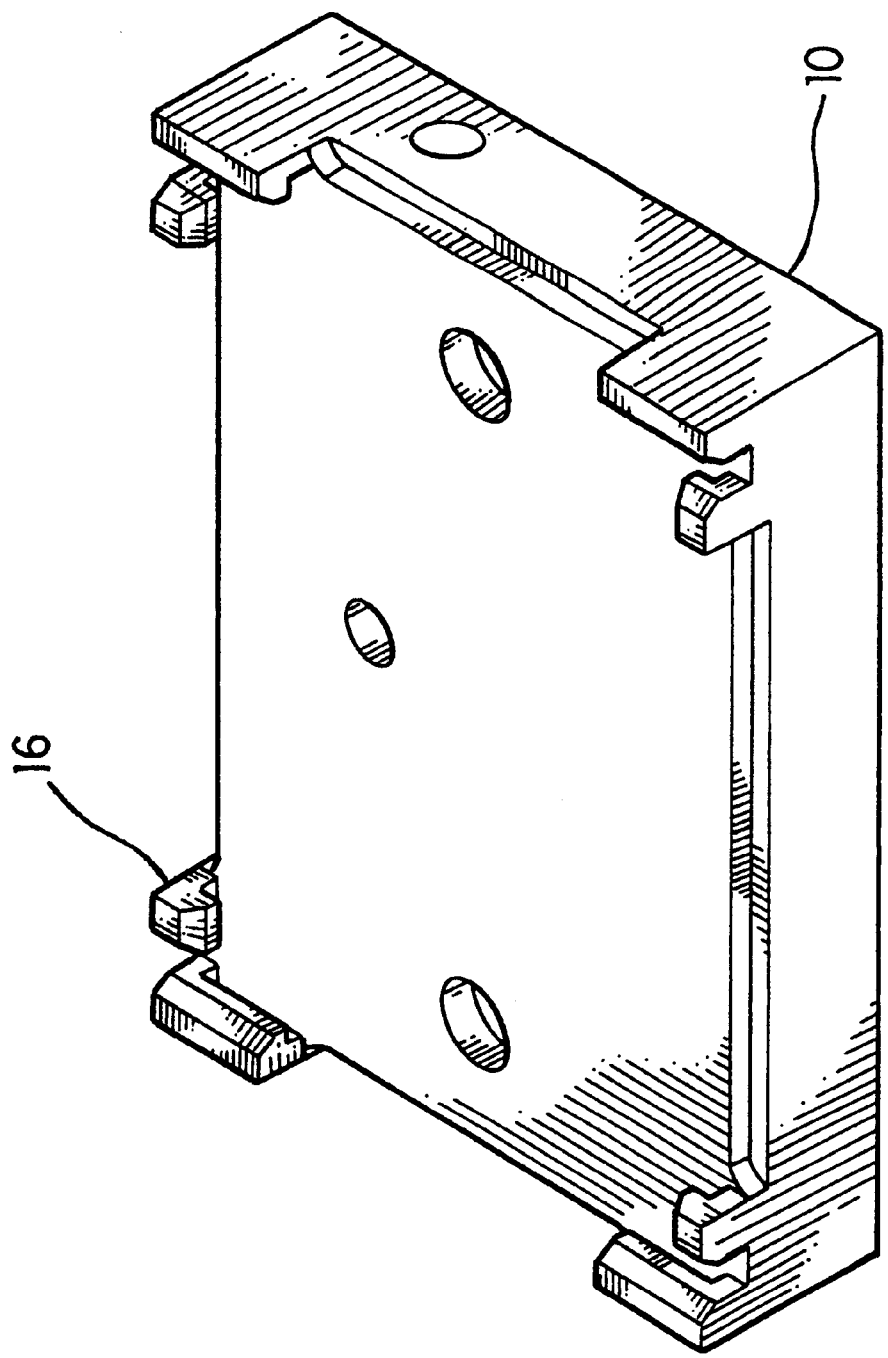
FIG. 3 is an isometric view in elevation of the gripping apparatus, wherein the raised, vertical edges, apertures, and attachment means are shown.

Referring to FIG. 3, an isometric view of the apparatus illustrates the raised edges 16 proximal to the corners of gripping apparatus 10, wherein the edges have a height greater than the base. Generally, these raised edges will exhibit a height of at least about one-half or greater than the height of the microplate placed thereon. Typically, the raised edges of the base will possess inwardly angled chamfers, wherein the chamfers will angle downward towards the top of the base at an angle of from about 30° to about 60°; preferably the chamfers will be at an angle of about 45°. Preferably, the height of the lower side of the chamfer edge will partially extend up the side of the top of the microplate. Since the robotic fingers will not always release the microplate exactly within the raised edges, the chamfered, raised edges are designed to guide the microplate down onto the apparatus after the robotic fingers release the plate.

Figure 4:
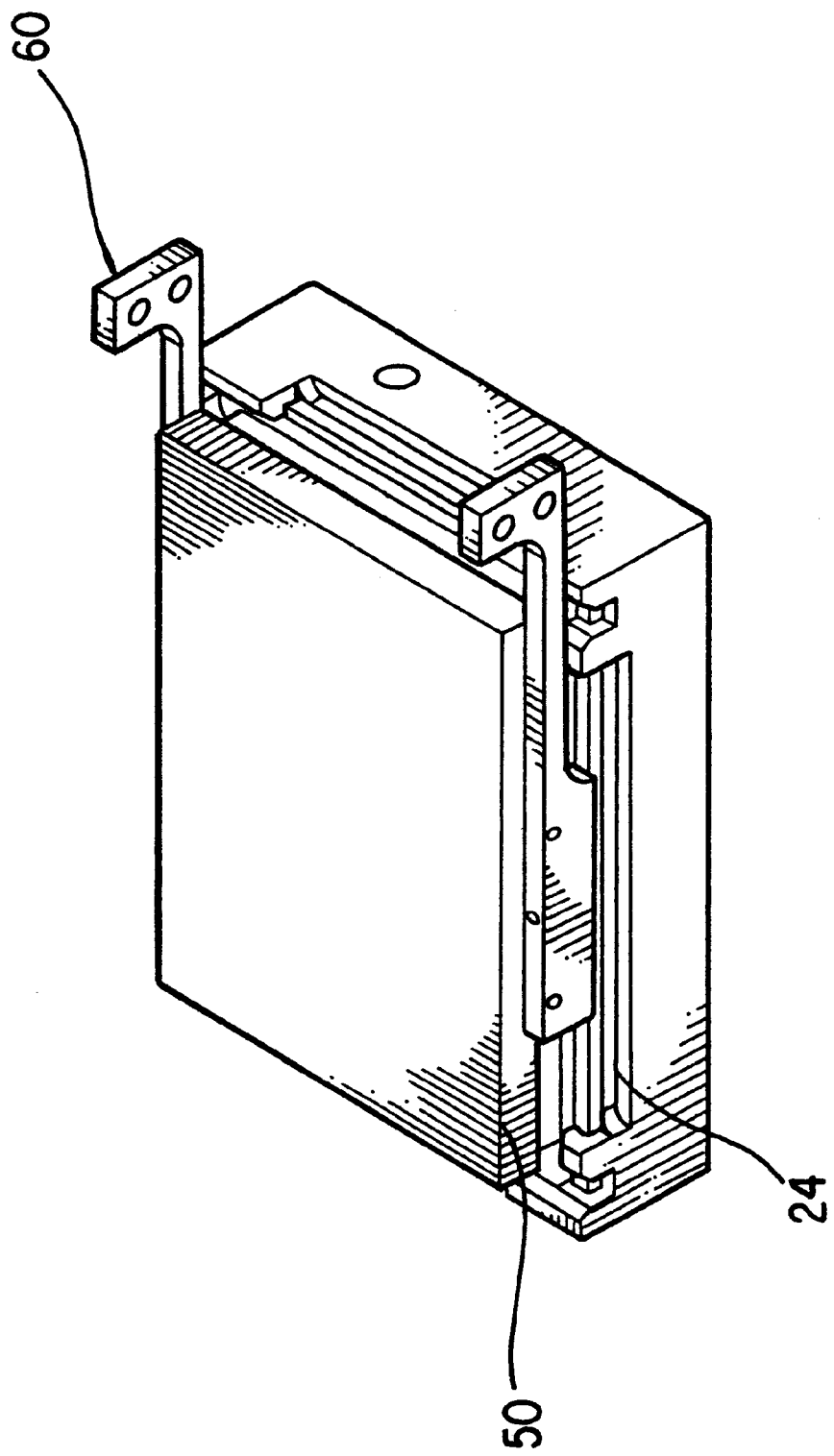
FIG. 4 is an isometric view in elevation of a lidded microplate resting on the apparatus, wherein the robotic fingers are positioned against the plate.

Referring to FIG. 4, there is illustrated an isometric view in elevation of lidded microplate 10 resting on the gripping apparatus. Ledges 24, defined as the horizontal spacing between the vertical edges of base and vertical edges of the plate gasket, are shown as being adjacent to the outer perimeter of the base. These ledges are adapted for abutting and protecting robotic fingers 60 from damage if the fingers are mis-aligned as they deliver and retrieve the microplate. Generally, the surface area dimensions of the microplate and base (within the raised edges) should be similar so that the microplate will fit on top of the plate gasket without any overhang. Typically, the robotic fingers should be about equal to the thickness of the plate gasket. Thus, during the operation of delivering and retrieving the microplate, the leading edge of the bottom of the fingers will align with the outer vertical edge of the plate gasket.

Generally, the plate gasket will be constructed of a flexible, resilient material such as natural and synthetic rubbers, nitrile, ethylene-propylene-diene monomer, silicon or thermoplastic elastomers. Suitable thermoplastic elastomers will include polypropylene, polyethylene and polyurethane. Generally, the base of the apparatus will be constructed of a solid, non-flexible material such a metals or non-elastic, thermoplastic materials. The metallic material of constructions can consists of pure metals, e.g. copper, zinc, magnesium, etc., or alloys thereof, such as aluminum, brass, various steels, e.g. stainless steel. The thermoplastic materials can include polyvinylchloride, polyacetals, polycarbonates, polyamides, polyimides, and nylons.

The principles, preferred embodiments and modes of operation of the present invention have been described in the foregoing specification. However, the invention disclosed and intended to be protected is not to be construed as limited to the particular embodiments disclosed. The embodiments are to be construed as illustrative rather than restrictive. It is recognized, however, that departures may be made therefrom within the scope of the invention, and that obvious modifications may occur to a person skilled in the art.

What is claimed is:

1. An apparatus for gripping and holding a container during delidding, mixing or oscillating operations, comprising:
   a horizontally positioned, flat surface base comprising: a vertical aperture partially extending through the top of the base; a horizontal aperture extending through a side of the base and intersecting the vertical aperture; a plurality of intermittent, vertical, raised edges on the top of the base; and means for attaching the base to a support;
   a flat, elastic plate gasket, conforming to the shape of the base, resting on top of the base between the raised edges, the gasket having a vertical aperture therethrough aligning with the vertical aperture of the base, wherein the height of the raised edges extend above the height of the plate gasket; and
   vacuum means attached to the horizontal aperture on the side of the base,
   wherein the container having a lid thereon and conforming to the shape of the base being placed on top of the plate gasket, fitting within and abutting against the raised edges of the base, and a vacuum being applied to the base, the container is suctionally pulled down towards the base and securely held there without loss of vacuum while means for removing the lid is being applied thereto.

2. The apparatus according to claim 1, wherein the shape of the base conforms to the container, said base being selected from rectangular, square and oval shapes.

3. The apparatus according to claim 2, wherein the shape of the base is rectangular.

4. The apparatus according to claim 3, wherein the top of the raised edges of the base consist essentially of chamfers angling inwardly and down toward the base.

5. The apparatus according to claim 4, wherein the plurality of raised edges are located along the corners of the base.

6. The apparatus according to claim 5, wherein the plate gasket is constructed from an elastic material selected from rubbers, silicon, and thermoplastic elastomers.

7. The apparatus according to claim 6, wherein the plate gasket is constructed from silicon.

8. The apparatus according to claim 7, wherein the chamfers of the raised edges are angled at about 45°.

9. The apparatus according to claim 8, wherein the vacuum means is a vacuum pump.

10. The apparatus according to claim 9, wherein the container is selected from the group consisting of a microplate, jar, vale and dish.

11. The apparatus according to claim 10, wherein the top of the raised edges of the base consist essentially of chamfers angling inwardly and down toward the base.

12. The apparatus according to claim 11, wherein the plate gasket is constructed from an elastic material selected from the group consisting of rubbers, silicon, and thermoplastic elastomers.

13. The apparatus according to claim 12, wherein the base is constructed from a material selected from the group consisting of metals and thermoplastic polymers.

14. The apparatus according to claim 13, wherein the vacuum means is a vacuum pump.

15. The apparatus according to claim 14, wherein the horizontal, outer ledges of the base are suitably adapted for the robotic fingers holding the microplate to be within proximal distance to the ledges while lowering and releasing the microplate onto the apparatus.

16. An apparatus for gripping a rectangular-shaped, microplate having a lid attached thereto during de-lidding operations by robotic fingers, comprising:

a horizontally positioned, rectangular-shaped, base having sides comprising: a centrally positioned, vertical aperture partially extending through the top of the base; a horizontal aperture partially extending through a side of the base and intersecting the vertical aperture to form a conduit; vertical, raised edges along the corners of the top of the base; and means for attaching the base to a support;

a flat, rectangular-shaped, elastic, plate gasket resting on top of the base having vertical edges and a vertical aperture therethrough aligning with the vertical aperture of the base, wherein the shape of the plate gasket conforms to and fits within the shape of the top of the base, the height of the vertical, raised edges extending above the height of the plate gasket, and horizontal, outer ledges formed along the sides of the base between the vertical edges of the plate gasket and the vertical, raised edges of the base; and vacuum means attached to the horizontal aperture on the side of the base, wherein the lid of the microplate having bottom edges protruding from the side of the plate, being held on opposing sides by robotic fingers while being placed on top of the plate gasket, the fingers being proximal to the ledges of the base and edges of the plate gasket, the microplate fitting within and abutting against the raised edges, a vacuum being drawn on the base, the microplate is suctionally pulled towards the base and securely held there without loss of vacuum, the robotic fingers releasing the microplate, and the fingers being raised to contact the protruding, bottom edges of the lid, and the robotic fingers being raised to remove the lid.

17. The apparatus according to claim 16, wherein the chamfers of the raised edges are angled at 45°.

18. The apparatus according to claim 17, wherein the plate gasket is constructed from silicon.

19. The apparatus according to claim 18, wherein the base is constructed from metal.

20. The apparatus according to claim 19, wherein the vacuum means is operated by a computer controlled solenoid valve.

* * * * *